United States Patent [19]
Takasu

[11] Patent Number: 5,236,414
[45] Date of Patent: Aug. 17, 1993

[54] FAT SUCKING APPARATUS

[76] Inventor: Katsuya Takasu, 124-1, Aza-kamigochu, Oaza-akabane, Ishiki-cho, Hazu-gun, Aichi-ken, Japan

[21] Appl. No.: 753,598

[22] Filed: Sep. 3, 1991

[30] Foreign Application Priority Data
Apr. 19, 1991 [JP] Japan ................... 3-117007

[51] Int. Cl.⁵ .............................................. A61B 17/20
[52] U.S. Cl. ..................................... 604/22; 604/902; 128/24 AA
[58] Field of Search ...................... 604/22, 35, 73, 902; 128/24 AA; 606/169-171

[56] References Cited
U.S. PATENT DOCUMENTS

| | | | |
|---|---|---|---|
| 3,810,471 | 5/1974 | Truhan | 604/902 |
| 4,504,264 | 3/1985 | Kelman | 604/35 |
| 4,516,395 | 5/1985 | Wuchinich | 128/24 AA |
| 4,767,404 | 8/1988 | Renton | 604/902 |
| 4,815,462 | 3/1989 | Clark | 604/22 |
| 4,867,747 | 9/1989 | Yarger | 604/902 |
| 4,886,491 | 12/1989 | Parisi et al. | 604/22 |
| 4,931,047 | 6/1990 | Broadwin et al. | 604/25 |
| 4,932,935 | 6/1990 | Swartz | 604/902 |
| 5,061,238 | 10/1991 | Shuler | 604/22 |
| 5,123,903 | 6/1992 | Quaid et al. | 406/169 |

Primary Examiner—Stephen C. Pellegrino
Assistant Examiner—Michael Rata
Attorney, Agent, or Firm—Armstrong, Westerman, Hattori, McLeland & Naughton

[57] ABSTRACT

A fat sucking apparatus including a tip having a tubular body which defines therein a suction passage and which has at least one suction opening at the front lower end of the tubular body, a hand piece to which the tip is detachably connected and which has therein a suction passage which is connected to the suction passage of the tip, said hand piece being provided with an ultrasonic oscillation generating portion which transmits the ultrasonic oscillation to the tip, an outer tube in which the tip is slidably inserted and held and which is provided with at least one suction opening, an ultrasonic oscillator which generates and transmits an electric energy to the ultrasonic oscillation generating portion of the hand piece to supply it with the ultrasonic oscillation, a collector which is connected to the suction passage of the hand piece through a suction pipe to receive the fat, and a vacuum pump which is connected to the collector to suck the fat into the collector.

17 Claims, 3 Drawing Sheets

5,236,414

FAT SUCKING APPARATUS

BACKGROUND OF THE INVENTION

1. Field of the Invention

The present invention relates to an apparatus for sucking fat and a fat sucking tool used in the apparatus.

2. Description of Related Art

For instance, in a cosmetic surgery, to remove the fat, a hollow tubular cannula is inserted into the subcutaneous tissue and is then moved in the subcutaneous tissue to crush the fat, so that the crushed fat is sucked outward by a vacuum pump or the like through a suction passage formed in the cannula.

However, in the known method, there are drawbacks as follows:

(a) it is necessary for an operator to carefully and troublesomely move the cannula in the subcutaneous tissue to mechanically crush or destroy the latter;

(b) it is difficult to precisely remove the fat at a predetermined position by the cannula which is manually moved by an operator, thus resulting in a decrease in scientific reliability;

(c) there is a large possibility that a soft tissue other than fat can be injured by the insertion and movement of the cannula; and, (d) it is difficult to control the bleeding from a cannula insertion portion of the human body and the soft tissue, injured by the cannula.

The primary object of the present invention is to eliminate the drawbacks mentioned above by providing a fat sucking apparatus in which the fat can be precisely and simply removed from the human body at a desired position thereof and in which the soft tissue other than the fat is prevented from being injured and the bleeding is extremely decreased.

SUMMARY OF THE INVENTION

To achieve the object of the present invention as mentioned above, there is provided a fat sucking apparatus comprising a tip having a tubular body which defines therein a suction passage and which has at least one suction opening at the front lower end of the tubular body, a hand piece to which the tip is detachably connected and which has therein a suction passage which is connected to the suction passage of the tip, said hand piece being provided with an ultrasonic oscillation generating portion which transmits the ultrasonic oscillation to the tip, an outer tube in which the tip is slidably inserted and held, and which is provided with at least one suction opening, an ultrasonic oscillator which generates and transmits an electric energy to the ultrasonic oscillation generating portion of the hand piece to supply it with the ultrasonic oscillation, a collector which is connected to the suction passage of the hand piece through a suction pipe to receive the fat, and a vacuum pump which is connected to the collector to suck the fat into the collector.

According to another aspect of the present invention, there is provided a fat sucking tool comprising a cannula comprising a tip having a tubular body which defines therein a suction passage and which has at least one suction opening at the front lower end of the tubular body, and a hand piece to which the tip is detachably connected and which has therein a suction passage which is connected to the suction passage of the tip, said hand piece being provided with an ultrasonic oscillation generating portion which transmits the ultrasonic oscillation to the tip, and an outer tube in which the tip is slidably inserted and held, and which is provided with at least one suction opening.

BRIEF DESCRIPTION OF THE DRAWINGS

The invention will be described below in detail with reference to the accompanying drawings, in which.

DESCRIPTION OF THE PREFERRED EMBODIMENTS

Figure 1:
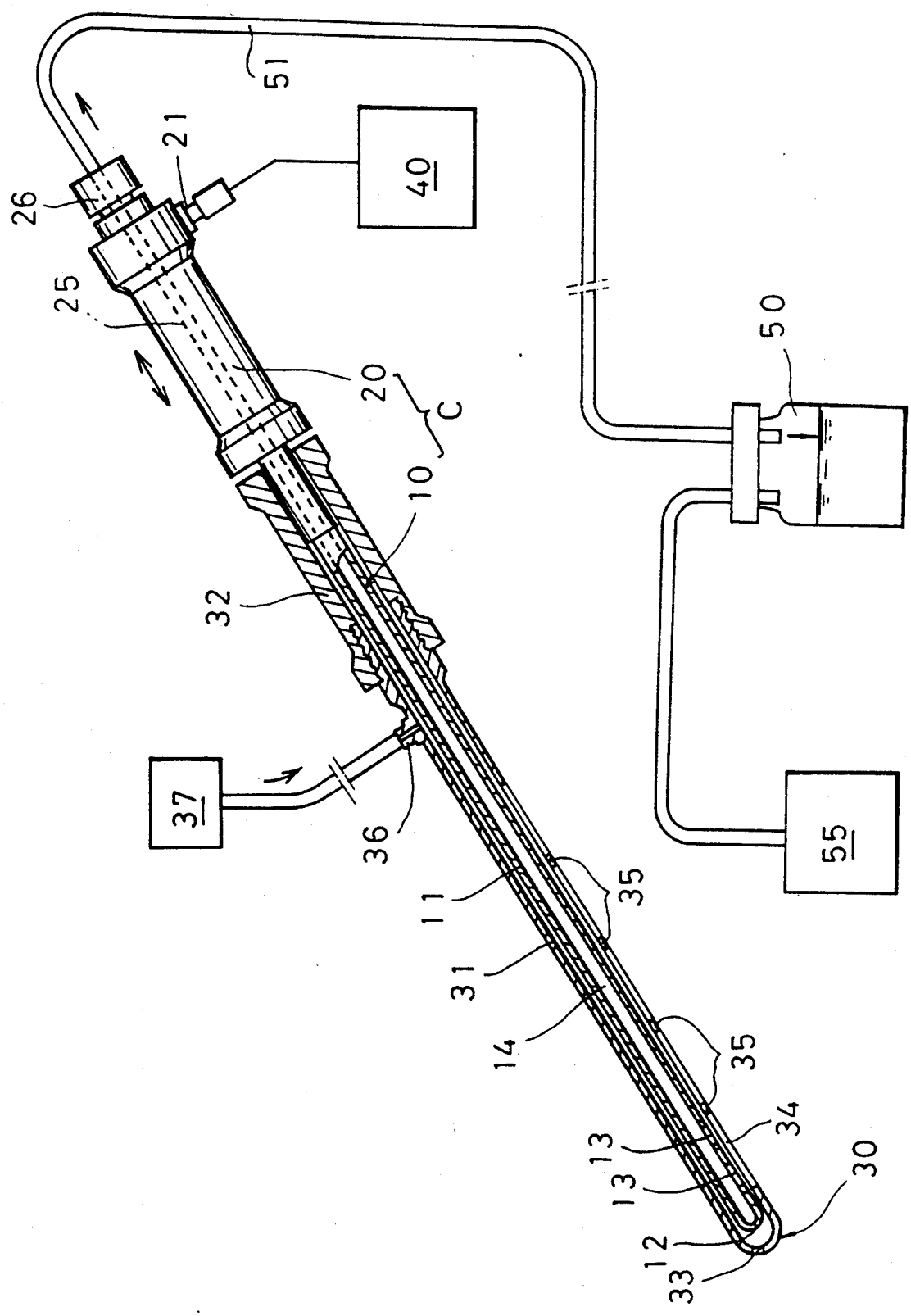
FIG. 1 is a partially sectioned side elevational view of a fat sucking apparatus according to an aspect of the present invention.

As can be seen from FIG. 1, the fat sucking apparatus of the present invention basically includes a tip 10, a hand piece 20, an outer tube 30 and an ultrasonic oscillator 40.

Figure 2:
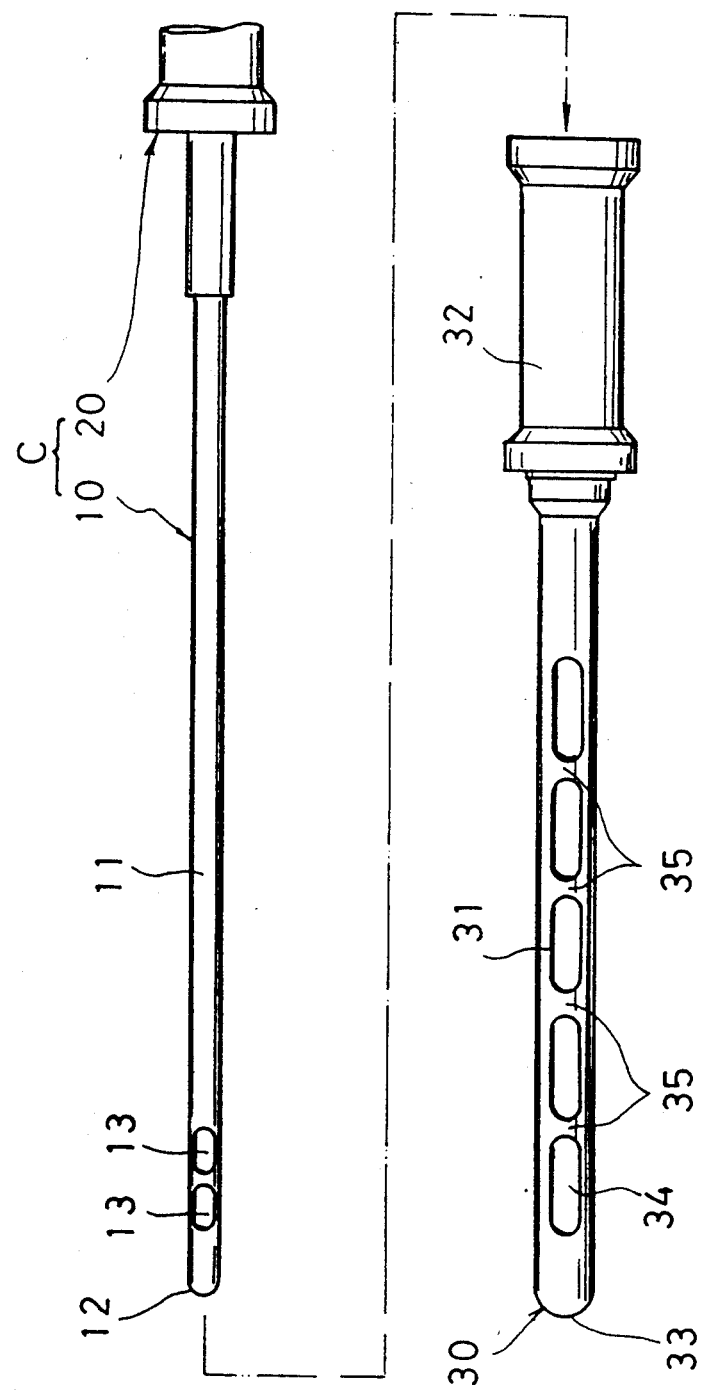
FIG. 2 is a schematic bottom view of a tip and an outer tube of a fat sucking apparatus shown in FIG. 1.

The tip 10 has a tubular body 11 of metal, such as titanium. The tip 10 is provided with a rounded front end 12 and sucking openings 13, 13 on the lower surface of the tube in the vicinity of the front end 12, as can be seen in FIG. 2. The tubular body 11 defines therein a suction passage 14 through which the crushed fat is sucked. In the illustrated embodiment, the tip 10 has 5 mm diameter and about 500 mm length.

The hand piece 20 is held by an operator to manually actuate the apparatus. The tip 10 is detachably connected to the front end of the hand piece 20. The hand piece 20 has an oscillation generating portion 21 and a suction passage 25.

The oscillation generating portion 21 is connected to an ultrasonic oscillator 40, so that the electric energy from the oscillator 40 is converted to the supersonic oscillation which is then transmitted to the tip 10 attached to the hand piece 20.

For instance, in the illustrated embodiment, the oscillation generating portion 21 generates the supersonic oscillation of 300 μm amplitude and 24000/sec. frequency.

The suction passage 25 is connected at its front end to the suction passage 12 of the tip 10 and at the rear end thereof to a front suction pipe 51 of the sucker 50, respectively. Numeral 26 designates a connecting portion of the suction pipe 51.

The tip 10 is slidably inserted and supported in an outer tube 30. The outer tube 30 is made of light plastics having a high heat-resistance, such as fluoroplastics or the like. The outer tube 30 is comprised of a tubular body 31 which is inserted in the subcutaneous tissue and a grip portion 32 which is held by an operator.

The tubular body 31 protects the soft tissue from the movement of the tip 20 and heat due to the supersonic oscillation. The tubular body 31 also contributes to a precise removal of the fat at a predetermined position from the human body. The front end 33 of the tubular body 31 is rounded to prevent the skin and the subcutaneous tissue from being injured upon insertion of the tubular body. The tubular body 31 is provided on the lower surface thereof with an appropriate number of sucking openings 34 aligned along the length thereof, as shown in FIG. 2. Numeral 35 designates reinforcing bridge portions between the sucking openings 64. In the illustrated embodiment, the tubular body 31 has 10 mm diameter and about 340 mm length.

As can be seen in FIG. 1, the tubular body 31 is provided on its base end with a water supplying port 36 through which a coolant is fed from a coolant source 37 into the tubular body 31 to cool the heat produced in the tip 10, in accordance with need. The coolant is sucked together with the crushed fat. For example, a balanced saline solution or the like can be used as a coolant.

The tubular body 31 is screwed in and connected to the front end of the grip 32. The whole length of the outer tube 30 having the grip 32 and the tubular body 31 attached to the grip 32 is substantially equal to or slightly longer than the length of the tip 10.

The ultrasonic oscillator 40 supplies the oscillation generating portion 21 of the hand piece 20 with electric energy which can be converted to the ultrasonic oscillation. In the illustrated embodiment, the ultrasonic oscillator 40 has an electrostrictive strain vibrator PZT of 24 kHZ of frequency of vibration and 100 W of maximum output.

The collector 50 is connected to the suction passage 25 of the hand piece 20 through the suction pipe 51. The collector 50 is also connected to a vacuum pump 55, so that the crushed fat introduced into the suction pipe from the suction openings 13 of the tip 10 is forcedly sucked into the collector 50 by the vacuum pump 55.

Figure 3:
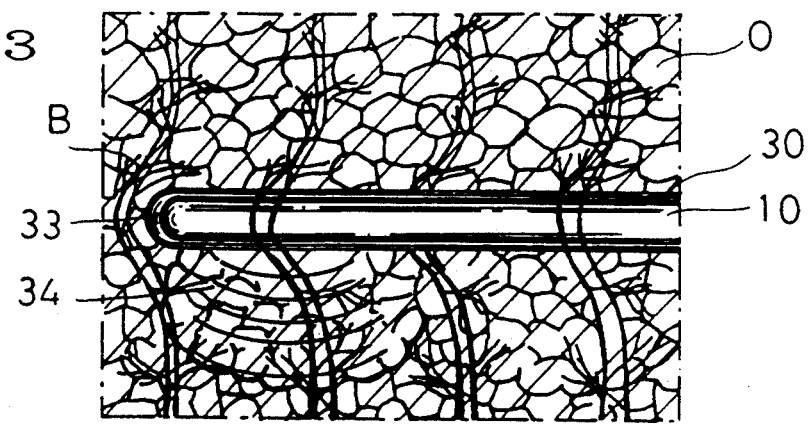
FIG. 3 is a partial schematic sectional view showing the insertion of a fat sucking apparatus into the subcutaneous tissue, according to the present invention.

The apparatus of the present invention operates as follows (see FIGS. 3 through 5).

First, a patient's skin is cut to a length enough to insert the front end of the outer tube 30, for example, about 10 mm, and then the front end of the outer tube 30 in which the tip 10 is held is inserted in the soft tissue O under the skin at a target portion in which the fat is to be removed through the cut portion of the patient's skin. Since the front end 33 of the outer tube 30 is rounded, the capillary B in the subcutaneous tissue is not injured by the outer tube 30.

Thereafter, the ultrasonic oscillator 40 is activated to transmit the ultrasonic oscillation to the tip 10 through the ultrasonic oscillation generating portion 21 of the hand piece 20. The tip 10 vibrates at a very high frequency, so that the fat tissue under the skin is crushed due to the vibration of the front end of the tip 10 through the suction openings 34 of the outer tube 30, as can be seen in FIG. 3. It should be appreciated that no vibration is transmitted to the tissue located above the outer tube 30, and accordingly, no destruction of the tissue immediately below the skin takes place.

Figure 4:
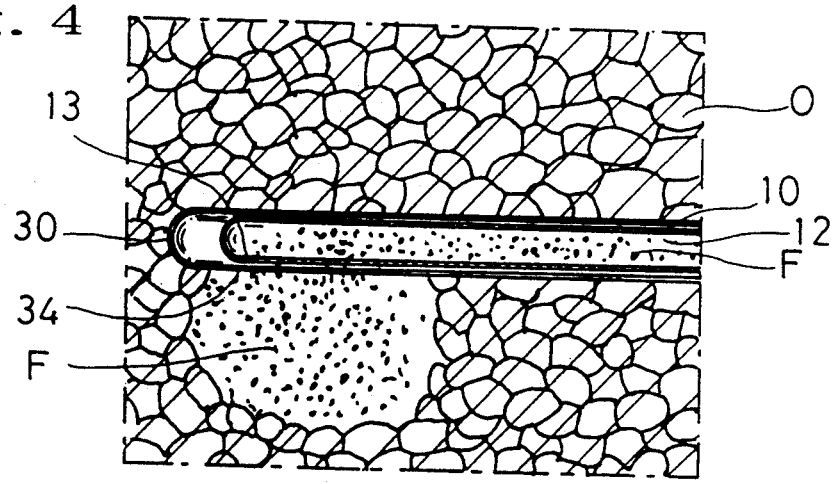
FIG. 4 is a partial schematic sectional view showing the ultrasonic oscillation crush of the subcutaneous tissue by a fat sucking apparatus, according to the present invention; and, FIG. 5 is a partial schematic sectional view showing the removal of the fat from the subcutaneous tissue, according to the present invention.
Figure 5:
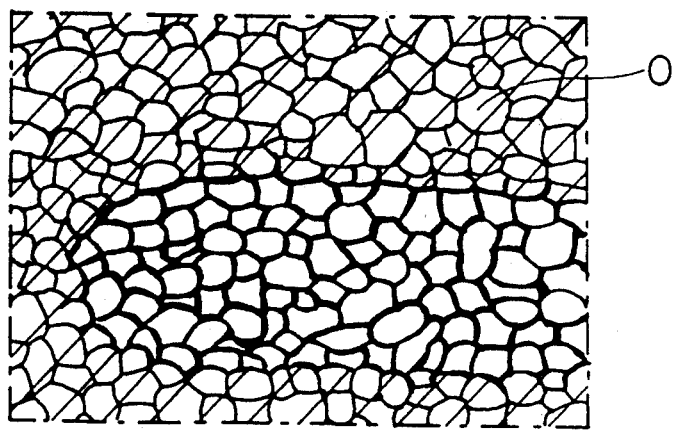

The fat F crushed by the ultrasonic oscillation is emulsified, as shown in FIG. 4, so that the fat F is sucked into the collector 50 through the suction openings 34 of the outer tube 30, the suction openings 13 of the tip 10, the suction passage 12 thereof and the suction pipe 51.

The tip 10 slides in the outer tube 30 to successively crush and suck the fat. If necessary, the operator continues with the fat suction operation while moving the outer tube 30. Thus, the fat is removed, as shown in FIG. 5.

According to the invention, since the subcutaneous fat is directly crushed by the ultrasonic oscillation of the crusher, the crushed fat is sucked and removed as it were melted butter. Accordingly, no mechanical crush or destruction of the fat tissue takes place, unlike the prior art, the bleeding can be controlled to be minimized.

Furthermore, since the tip slides in the outer tube, the soft tissue under the skin can be protected by the outer tube. In addition, the insertion opening cut in the skin is not subject to a friction, so long as the outer tube is not moved, and accordingly, the cut will only leave a scar substantially without bleeding.

Furthermore, since the tip smoothly slides in the outer tube, the labour of the operator can be largely reduced, and a precise removal operation can be expected.

Since the intensity and frequency of the ultrasonic wave of the ultrasonic oscillator can be simply and easily controlled, the necessary ultrasonic oscillation can be easily obtained.

I claim:

1. A fat sucking apparatus comprising:
   a tip having a tubular body which defines therein a suction passage and which has at least one suction opening at the front lower end of the tubular body;
   a hand piece to which the tip is detachably connected and which has therein a suction passage which is connected to the suction passage of the tip, said hand piece being provided with an ultrasonic oscillation generating portion which transmits the ultrasonic oscillation to the tip;
   an outer tube in which the tip is slidably inserted and held, and which is provided with a plurality of suction openings;
   means for moving said tip along the length of said outer tube when said apparatus is in use such that said tip suction portion can be disposed proximate to each of said plurality of suction openings of said outer tube;
   an ultrasonic oscillator which generates and transmits an electric energy to the ultrasonic oscillation generating portion of the hand piece to supply it with the ultrasonic oscillation;
   a collector which is connected to the suction passage of the hand piece through a suction pipe to receive the fat; and
   a vacuum pump which is connected to the collector to suck the fat into the collector.

2. A fat sucking apparatus according to claim 1, wherein said tip includes a tubular body which defines therein a suction passage and a grip to be held by an operator.

3. A fat sucking apparatus according to claim 2, wherein said outer tube has a rounded front end.

4. A fat sucking apparatus according to claim 3, further comprising a cooler for cooling the tip.

5. A fat sucking apparatus according to claim 1, wherein said outer tube is made of plastic having a high heat resistance.

6. A fat sucking apparatus according to claim 1, wherein said at least one suction opening of said tip comprises a plurality of suction openings.

7. A fat sucking apparatus according to claim 6, wherein said plurality of suction openings are disposed adjacent one another along the length of said tip at said front lower end of said tubular body, said plurality of tip suction openings defining a suction portion of said tip.

8. A fat sucking apparatus according to claim 7, wherein each of said plurality of suction openings of said outer tube has a length substantially corresponding to a length of said suction portion of said tip.

9. A fat sucking apparatus according to claim 8, wherein said plurality of suction openings of said tip comprises two adjacent tip suction openings within said suction portion of said tip.

10. A fat sucking tool comprising:
a cannula comprising a tip having a tubular body which defines therein a suction passage and which has at least one suction opening at the front lower end of the tubular body, and a hand piece to which the tip is detachably connected and which has therein a suction passage which is connected to the suction passage of the tip, said hand piece being provided with an ultrasonic oscillation generating portion which transmits the ultrasonic oscillation to the tip;
an outer tube in which the tip is slidably inserted and held, and which is provided with a plurality of suction openings;
and further comprising means for moving said tip along the length of said outer tube when said tool is in use such that said tip suction portion can be disposed proximate to each of said plurality of suction openings of said outer tube.

11. A fat sucking tool according to claim 10, wherein said at least one suction opening of said tip comprises a plurality of suction openings.

12. A fat sucking tool according to claim 11, wherein said plurality of suction openings are disposed adjacent one another along the length of said tip at said front lower end of said tubular body, said plurality of tip suction openings defining a suction portion of said tip.

13. A fat sucking tool according to claim 12, wherein each of said plurality of suction openings of said outer tube has a length substantially corresponding to a length of said suction portion of said tip.

14. A fat sucking tool according to claim 13, wherein said plurality of suction openings of said tip comprises two adjacent tip suction openings within said suction portion of said tip.

15. A fat sucking tool comprising:
a cannula comprising a tip having a tubular body which defines therein a suction passage and which has at least one suction opening at the front lower end of the tubular body, and a hand piece to which the tip is detachably connected and which has therein a suction passage which is connected to the suction passage of the tip, said hand piece being provided with an ultrasonic oscillation generating portion which transmits the ultrasonic oscillation to the tip;
an outer tube in which the tip is slidably inserted and held, and which is provided with a plurality of suction opening; and
means for slidably moving said tip within and relative to said outer tube when said tool is in use so that said at least one suction opening of the tip is positionable proximate to each of said plurality of outer tube suction openings.

16. A fat sucking tool according to claim 15, wherein said at least one suction opening of said tip defines a suction portion of said tip, said suction portion of said tip having a length corresponding to a length of each of said plurality of outer tube suction openings.

17. A fat sucking tool according to claim 16, wherein said suction portion of said tip comprises a plurality of suction openings.

* * * * *